(12) United States Patent
Schneider et al.

(10) Patent No.: US 6,726,650 B2
(45) Date of Patent: *Apr. 27, 2004

(54) AUTOMATIC LIQUID INJECTION SYSTEM AND METHOD

(75) Inventors: Michel Schneider, Troinex (CH); Christophe Golay, Les Eplanes (CH); Laurent Jakob, Soral (CH); Jean Brochot, Feigeres (FR); Feng Yan, Meyrin (CH); Christian Mathieu, Remoray (FR)

(73) Assignee: Bracco Research S.A., Geneva (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/204,067

(22) Filed: Dec. 3, 1998

(65) Prior Publication Data

US 2002/0077588 A1 Jun. 20, 2002

(30) Foreign Application Priority Data

Dec. 4, 1997 (EP) .............................................. 97810947

(51) Int. Cl.[7] .............................................. A61M 37/00
(52) U.S. Cl. ............................ 604/82; 600/432; 366/54
(58) Field of Search .................. 604/82, 131, 151–155, 604/118, 121, 186–188, 182, 181, 218, 224, 225, 235; 128/DIG. 1, 12; 424/9.3, 9.4, 9.5, 9.52; 600/431, 432; 366/53, 54, 92–93

(56) References Cited

U.S. PATENT DOCUMENTS

| | | | |
|---|---|---|---|
| 3,812,843 A | * | 5/1974 | Wooten et al. |
| 4,652,260 A | | 3/1987 | Fenton, Jr. et al. |
| 4,978,335 A | | 12/1990 | Arthur, III |
| 5,110,475 A | * | 5/1992 | Rossling et al. |
| 5,176,502 A | | 1/1993 | Sanderson et al. |
| 5,176,646 A | | 1/1993 | Kuroda |
| 5,244,461 A | * | 9/1993 | Derlien |
| 5,317,506 A | | 5/1994 | Coutre et al. |
| 5,401,253 A | | 3/1995 | Reynolds |
| 5,528,923 A | | 6/1996 | Ledez et al. |
| 5,611,344 A | | 3/1997 | Bernstein et al. |
| 5,647,851 A | * | 7/1997 | Pokras |
| 5,686,060 A | * | 11/1997 | Schneider et al. |
| 5,690,618 A | | 11/1997 | Smith et al. |
| 5,772,443 A | * | 6/1998 | Lampotang et al. |
| 5,806,519 A | | 9/1998 | Evan, III et al. |
| 5,840,026 A | | 11/1998 | Uber, III et al. |

(List continued on next page.)

FOREIGN PATENT DOCUMENTS

| | | |
|---|---|---|
| WO | WO 96/18420 | 6/1996 |
| WO | WO 00/12157 | 3/2000 |
| WO | WO 00/12158 | 3/2000 |
| WO | WO 00/53242 | 9/2000 |
| WO | WO 00/71189 | 11/2000 |

OTHER PUBLICATIONS

Owens et al Am. J. Health–Syst. Pharmacists, vol. 54 3/97 pp 683–686 XP002064707 Stability of amphotericin B 0.05 and 0.5 mg/mL in 20% fat emulsion 1.

Primary Examiner—LoAn H. Thanh
(74) Attorney, Agent, or Firm—Kramer, Levin, Naftalis & Frankel LLP

(57) ABSTRACT

A power assisted method and injector device for controllably delivering to patients a dispersion medicament or diagnostically active agent, the homogeneity of which is preserved throughout delivery. Diagnostically active agents disclosed are gas microbubble suspensions useful in ultrasonic diagnostic imaging and liposomal formulations in which liposome vesicles are loaded with iodinated compounds.

31 Claims, 4 Drawing Sheets

U.S. PATENT DOCUMENTS

| | | |
|---|---|---|
| 5,896,804 A | 4/1999 | Kimura et al. |
| 5,997,502 A | 12/1999 | Reilly et al. |
| 6,063,052 A | 5/2000 | Uber, III et al. |
| 6,090,064 A | 7/2000 | Reilly et al. |
| 6,317,623 B1 | 11/2001 | Griffiths et al. |
| 6,402,717 B1 | 6/2002 | Reilly et al. |
| 6,402,718 B1 | 6/2002 | Reilly et al. |
| 2002/0040208 A1 | 4/2002 | Flaherty et al. |
| 2002/0072733 A1 | 6/2002 | Flaherty |
| 2002/0077588 A1 | 6/2002 | Schneider et al. |

* cited by examiner

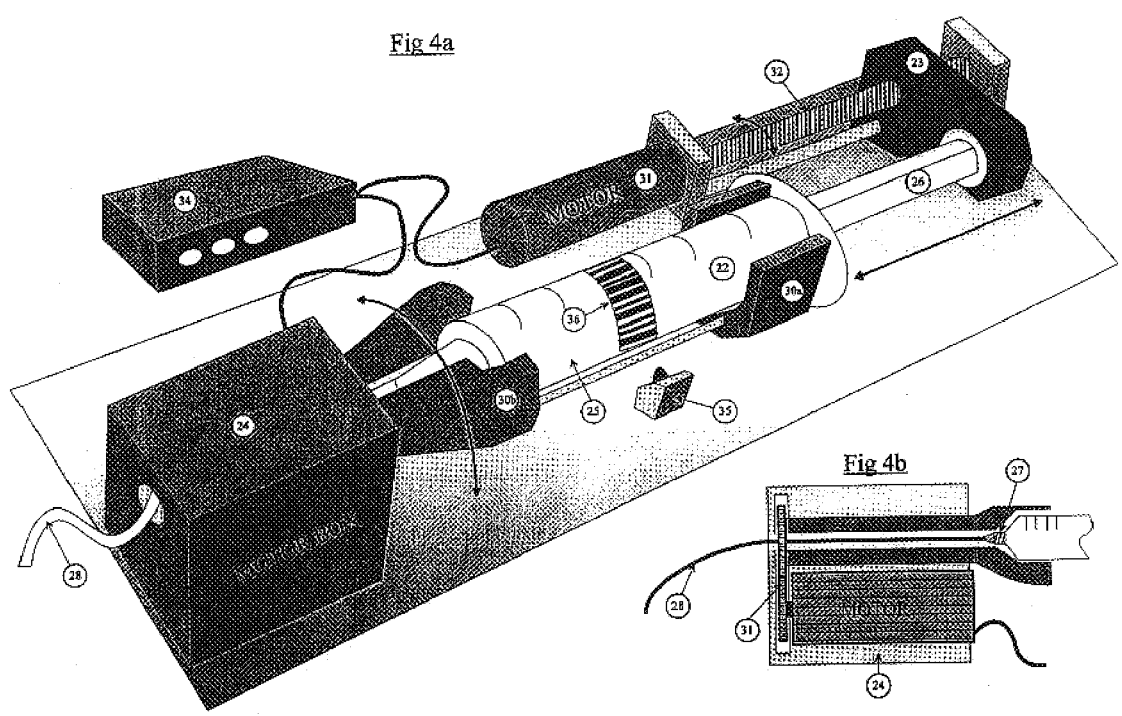

AUTOMATIC LIQUID INJECTION SYSTEM AND METHOD

FIELD OF THE INVENTION

The present invention concerns the administration by injection to patients of liquid compositions for therapeutic or diagnostic purposes. It more particularly concerns a power assisted method and device for controllably dispensing a liquid medicament or diagnostically active contrast agent, the homogeneity of which is preserved throughout delivery. Typically, the contrast agent is an aqueous suspension of gas filled microvesicles, namely microbubbles bounded by a surfactant stabilized gas/liquid interface, or microballoons bounded by a tangible material envelope.

BACKGROUND ART

Power injectors and mechanically assisted infusion systems for controllably dispensing therapeutically active medications are well known in the art. Typically, such devices include an automatic injector for syringes containing an injectable liquid and a plunger or piston movable within the barrel of the syringe to expel said liquid through a tip thereof and injecting into a patient via a tubing connected to an injecting needle or catheter. For controlling the injections parameters, the plunger is driven by means of an electro-mechanical arrangement organised to push the plunger at a desired rate, continuously or at chosen intervals, so that the amount of medication is delivered to the patient's body under strictly determined conditions. For instance, in the case of intravenous dispensing contrast agent formulations for diagnostic purposes (X-ray, MRI or ultrasound), the rate and the mode of injection can be accurately controlled to match the requirements of the imaging methods and detector systems used to investigate the circulation or a specific organ in the body. Typical automated injection devices are illustrated and described in U.S. Pat. No. 5,176,646 incorporated herein by reference.

Although the automated injectors known are highly sophisticated instruments capable of mastering most injection problems experienced in practice, there remains at least one variable factor not yet under control. Indeed the known power injectors have no control of the homogeneity of the liquid stored within the syringe barrel during the course of its application. This kind of problem is of course non-existent with "true solutions" (i.e. solutions to the molecular level) since in this case no concentration change can occur in the course of time; it however may become important when the injectable formulation is a suspension or dispersion of active particles which tend to settle, coalesce or segregate with time in the syringe. Indeed, even some modest separation of the particles by gravity or otherwise from the carrier liquid in the course of administration of the formulation may have very important influence on reproducibility and reliability of the tests. Hence, in this case, a method and means to keep the syringe content homogeneous during injection is highly desirable. The present method and device constitute a very effective solution to the aforediscussed problem.

SUMMARY OF THE INVENTION

Briefly stated, in order to secure homogeneity of a liquid suspension of particles within the barrel of an injector device, the invention provides a method and means whereby the particles are kept under sufficient agitation so as not to settle, segregate or agglomerate in the carrier liquid. This may involve acting on the carrier liquid itself, i.e. on the bulk of the suspension, or may involve acting only on the particles (in this case, one would expect the moving particles to impart motion to the carrier liquid by viscous friction). The agitation means may be provided within the syringe or in some cases outside thereof; for instance with magnetic particles, the particles can be subjected to an external variable magnetic field, the oscillation or rotation of which will set them into motion, the moving particles then acting on the carrier liquid and keeping the suspension homogeneous.

In the case of particles not sensitive to external fields, mechanical agitation is provided to the extent that it is sufficient to keep the suspension homogeneous but insufficient to break or damage the particles or disturb their distribution. For this, the syringe barrel may be subjected to motion, said motion being continuous or discontinuous, regular or irregular; the motion can possibly have a shaking, rocking or oscillating effect on the syringe. The frequency, intensity and rate of the motion is such that it will not interfere with the control of delivery parameters of the suspension.

The embodiments disclosed below in connection with the annexed drawings provides very effective means to keep the syringe content under sufficient agitation to secure injection of a homogeneous therapeutic or diagnostic liquid compositions into a patient.

BRIEF DESCRIPTION OF THE DRAWINGS

FIG. 4a is a schematic view in perspective of another device for agitating a liquid within the syringe of a power driven automatic injector system of the invention. In this embodiment, the syringe is held by a supporting bracket, the latter being driven into motion by a motor.

FIG. 4b is a schematical sectional view of the motor driving means of the embodiment of FIG. 4a.

DETAILED DESCRIPTION OF THE INVENTION

Figure 1:
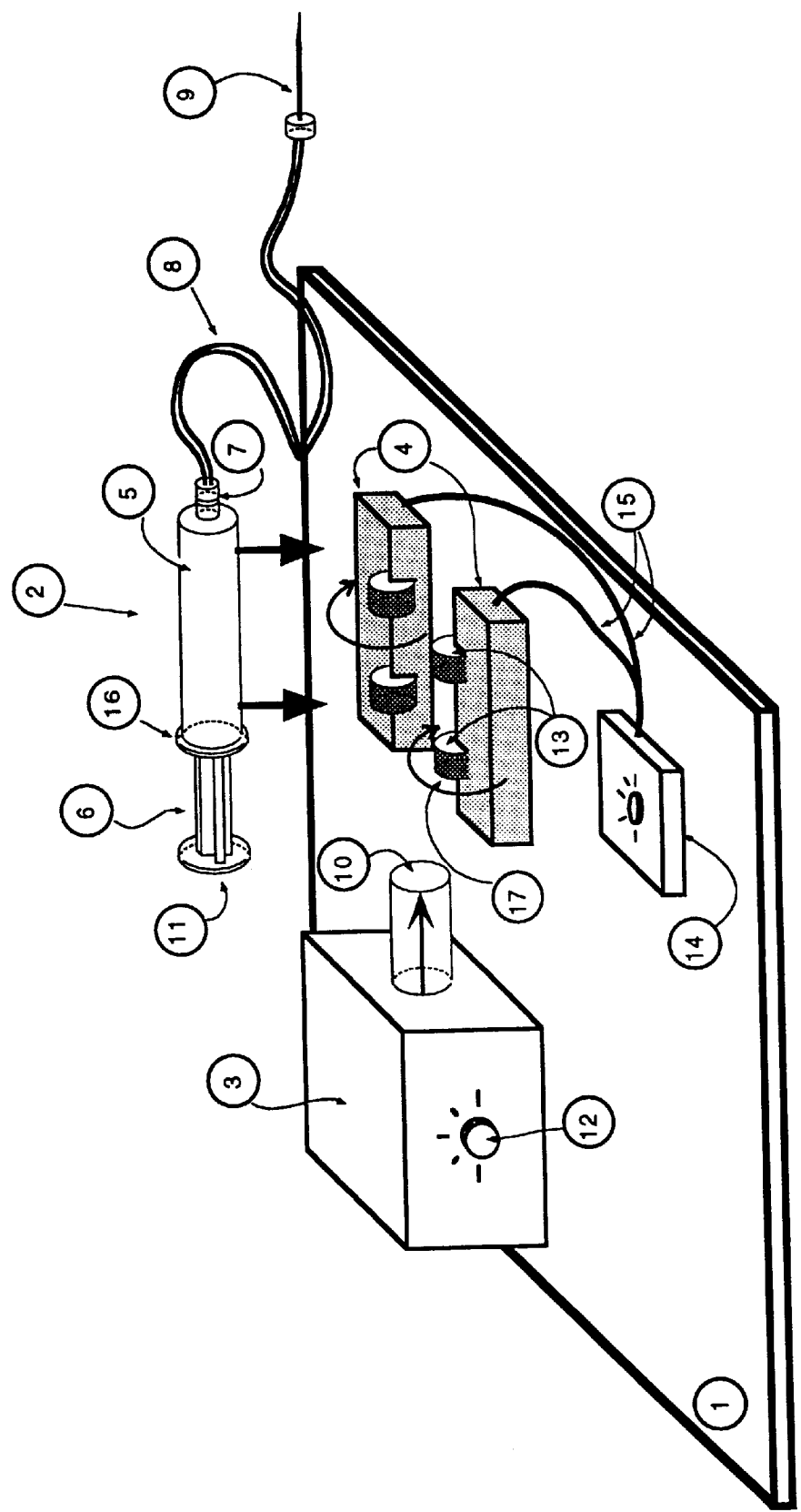
FIG. 1 is a schematic view in perspective of a device for agitating a liquid within the syringe of a power driven automatic injector system of the invention.

The device represented schematically in FIG. 1 comprises a series of co-operating elements mounted on a board 1. Such schematic representation of the present device is only for clarity and better understanding of the device's operation. Obviously, in its actual commercial construction, the device is in the form of a much more compact and sophisticated apparatus, for instance in the form of an instrument like the Perfusor® fm of the Firm BRAUN Meslungen AG, D-34209, Meslungen, Germany (displayed in Publication B.03.01.95 No 0879 0744), or like the apparatuses disclosed in U.S. Pat. No. 4,652,260 and U.S. Pat. No. 5,176,502, both being incorporated herein by reference.

The present device comprises the following working components: a syringe 2 shown in an uplifted position, an automatic power driving unit 3 for acting on the syringe, a pair of syringe motioning units 4 for liquid agitation, and a control box 14 for controlling operation of the units 4.

The syringe 2 has a barrel 5, a plunger 6 sliding in the barrel and a tip connector 7 linked to a tubing 8, the latter leading to an injection needle 9. The needle 9 is for injecting an administrable liquid into the tissues or the circulation of a patient.

The power driving unit 3 has an electromechanically controlled pusher rod 10 for acting on the rear end 11 of the syringe plunger, and a control knob 12 for setting the automatic driving parameters that will rule the action of the rod 10. As such, the automatic electromechanical power means in this embodiment can be provided by, inter alia, the automatic power driving unit 3, including the electromechanically controlled pusher rod 10 and the control knob 12.

Each unit 4 is equipped with two rollers 13, themselves driven into rotation by electric motors within the units and not represented in the drawing. The rotation of the rollers 13 is governed by means of a box 14 via lead wires 15 connected to said motors. As such, means for continuously rocking or rotating said syringe in this embodiment can be provided by, inter alia, the unit 4 including the rollers 13 and/or box 14 govening the rotation thereof. The rollers 13 further can provide support means for this embodiment.

In operation, an injectable carrier liquid with particles (e.g. gas-filled microballoons) in suspension is introduced into the barrel 5 of the syringe 2 through the tip 7, this being consecutive to the retraction (manual or mechanical) of the plunger 6, so that an adequate pumping action is provided. Then the syringe is placed on the rollers 13, so that the flange 16 thereof abuts the roller's edge 17, this being for retaining the syringe in its relative position against unwanted longitudinal translation. In this situation, the pushing rod 10 of the driving unit 3 couples with the plunger's end 11, so that any forward displacement of the rod 10 is transferred to the plunger with consequent expelling of the liquid toward the needle 9 for injection.

During injection, the rollers will alternately rotate the syringe a certain angle in one direction, say 30°, 60°, 90°, 180°, 270° or 360° and then, reciprocably, in the opposite direction. This balancing motion, which may be carried out in a stepwise manner, will move the liquid carrier to such an extent that any separation or segregation of the particles is hindered. This is very efficient for instance in the case of suspensions of gas-filled microbubbles used in echography since there is always a bubble size distribution in such suspensions, the larger bubbles tending to rise faster than the smaller ones by buoyancy. In a variant, the syringe can be made to rotate in one direction only, provided that the connector tip 7 thereof is made to freely rotate in order to prevent distortion of the tubing 8. Normally, the rate of rotation impressed by the rollers 13 is from about 0.5 to 200 rpm depending upon the suspension viscosity. This rate should be sufficient to keep the particles in homogeneous suspension but insufficient to break the particles or disturb their distribution in the carrier liquid. If necessary, in the case of more viscous suspensions, an additional vibrational motion of a few Hz to a few hundreds of Hz can be applied to the syringe by means of a pitch-fork or pitch-pipe. It should be mentioned that at very high rotation rates (e.g. 1,000 rpm or more) the radial speed may become dominant which will result in axial concentration of the microbubbles in the middle of the syringe. Rotational speeds at which the radial component becomes important are to be avoided as under such conditions the suspension will become non-homogeneous again. This is clearly undesired.

In a variant, the unit 4 can have the form of a closable housing equipped with fixed syringe retaining means, i.e. other than the rollers edges 17 and, possibly if required, pressure resisting means (like a pressure mantle or jacket) in case the suspension is viscous and exerts undue pressure efforts to the syringe barrel. These can also function as support means. Also the syringe components can be made of moulded plastic (disposable syringes) and the barrel external surface provided with an integrally moulded relief pattern mating with corresponding pattern on the roller's surface, so that positive grip drive of the syringe is ensured.

Also, the rod 10 and the plunger 6 can be made integral with each other so that filling of the syringe can be controlled by the power unit 3, the pumping action then resulting from a backward displacement of rod 10.

The power unit per se is standard and its nature and operation well known to the skilled person. Embodiments thereof are disclosed in the cited references and also in U.S. Pat. No. 5,456,670. The power unit usually contains an electrically powered and controlled helical screw means (e.g., a screw or shaft with a continuous external helical thread thereon which mates with interior threads of another component which permits the shaft to rotate about a longitudinal axis) for mechanically advancing or retracting rod 10 continuously or intermittently, so that the liquid in the syringe can be dispensed continuously or by increments. The various parameters ruling said motions of the syringe piston can be monitored and adjusted by the control 12 and possible other control means not represented in the drawing. Means of unit 3 also ensure that such delivery parameters can be monitored and recorded for display. An instant stop switch (not shown) may also exist, in case the operation of the system should be suddenly interrupted due to a problem with the patient or otherwise. The security means for automatically interrupting the injector operation can thus be provided by, inter alia, the power unit, control 12 or the stop switch.

It should be incidentally noted that although the present embodiment involves rocking the syringe only, one may also consider a modification involving a back and forth rotation of the pumping ensemble, this being achieved by well known mechanical means adapted to support said pumping ensemble and to impart motion thereto.

Furthermore, although the present embodiment involves motion around the longitudinal axis, a variant may include rocking the syringe about a transversal axis.

A second device embodiment illustrated schematically in FIGS. 4a and 4b comprises a syringe 22 with a a barrel 25 supported in a rotatable fashion by a bracket 30a–30b and a plunger 26 sliding in the barrel whose displacement therein is controlled by a a power driven unit 23 capable of moving forward and backward in engagement with the back pusher end of the plunger 26. The device also comprises a motor driven unit 24 encompassing a portion 30b of the supporting bracket, the latter being rotated through gears 31, as better shown on FIG. 4b, for agitation of a liquid suspension in the syringe barrel. The longitudinal forward or backward displacement of the unit 23 (acting on the plunger 26) is effected via a motor 31 which rotates a screw-bar 32, the latter engaging with a matching threaded portion (not shown) within the unit 23. The device further comprises an electronicaliy computerized control box 34 for controlling operation of the units 23 (via motor 31) and 24, and for processing the signals from a laser detector 35 designed to read an identifying mark 36 on the syringe; this mark is for preventing errors in the selection of the syringe, especially if the syringe is of the prefilled type. The code of the mark can be according to standard bar codes. Note in this regard that since the syringe barrel is set into rotation in the present device, one can use a fixed detector instead of a mobile one which is advantageous designwise. By counting and recording via box 24 the number of turns of the screw bar 32, the position of the unit 23 (and consequently of the plunger 26) can be monitored and regulated at will. The control box 34 can of course comprise further monitoring and visualizing means (not shown) to optically display and appropriately regulate the various parameters involved in operation of the device. As in the previous embodiment, the syringe has a tip 27 for connecting to a liquid dispensing tubing 28, the latter leading to means for injecting an administrable liquid into a patient. As such. the automatic electromechanical power means in this embodiment can be provided by, inter alia, any combination of the power unit 23, the motor driven unit 24, the plunger 26, the motor 31, the screw-bar 32, and/or the electronically computerized control box 34. Brackets 30a and/or 30b thus can provide the means for continuously rocking or rotating said syringe as well as the support means. Helical screw means can be provided by, inter alia, the power unit 23, motor 31, and/or the screw-bar 32.

The operation of the present device is very similar to that of the earlier embodiment and hence needs not be discussed further at length. Suffice to say that it may also comprise security means intended to automatically interrupt the operation in case troubles develop with the patient or otherwise during injection. For instance, the pressure in the syringe barrel can be monitored by registering the force required to push the plunger, this being via the power absorbed by the driving motor 31. A sudden surge, for instance a rapid increase of current in said motor can trigger via the control unit 34 an emergency stop of the device. Alternatively, this effect could also be detected according to usual means by a strain gauge installed in the drive 23. As such, the security means in this embodiment can be provided by control unit 34 and/or a strain gauge installed in drive 23.

As already said, the particles of the suspensions in this invention may be of various kinds and involve for instance microspheres containing entrapped air or other gases used in echography. These microspheres may be bounded by a liquid/gas interface (microbubbles), or they may have a tangible membrane envelope of for instance synthetic polylactides or natural polymer like denatured protein such as albumin (microballoons). The carrier liquid for the microbubble suspensions comprises surfactants, preferably saturated phospholipids in laminar or lamellar form such as diacylphosphatidyl derivatives in which the acyl group is a $C_{16}$ or higher fatty acid residue.

The gases used in the microbubbles or microballoons are pure gases or gas mixtures including at least one physiologically acceptable halogenated gas. This halogenated gas is preferably selected among $CF_4$, $C_2F_6$, $C_3F_8$, $C_4F_8$, $C_4F_{10}$, $C_5F_{12}$, $C_6F_{14}$ or $SF_6$. The gas mixtures can also contain gases such as air, oxygen, nitrogen, helium, xenon or carbon dioxide. In fact in a number of cases microbubbles or microballoons will contain mixtures of nitrogen or air with at least one perfluorinated gas in proportions which may vary between 1 and 99%.

In the microballoons the membrane is made from a biodegradable material such as biodegradable polymers, solid triglycerides or proteins and are preferably selected from the polymers of polylactic or polyglycolic acid and their copolymers, denatured serum albumin, denatured haemoglobin, lower alkyl polycyanoacrylates, and esters of polyglutamic and polyaspartic acid, tripalmitin or tristearin, etc. In an embodiment, the microballoons are filled with $C_3F_8$ and the material envelope is made of albumin.

Homogeneity of suspensions of microballoons whose membrane is made of saturated triglycerides such as tripalmitin, trimyristin or tristearin and their mixtures with other tri- or di-glycerides, fatty acids or polymers is particularly interesting as those are used for delivering active ingredients to specific sites within the body. Homogeneity of suspensions of such microballoons has been effectively maintained using the method and the device of the invention.

Other particles whose density is different from that of the carrier liquid may include liposomes filled with iodinated X-ray opacifiers such as iomeprol, iopamidol, iopentol, iohexol, metrizamide, iopromide, iogulamide, iosimide or ioversol or, for instance, coated and uncoated magnetic particles which tend to precipitate in saline or other carriers.

The present injector system can be used in imaging organs, blood vessels and tissues of mammalians, e.g. the ultrasonic imaging of the heart, the liver or spleen, the brain, the kidneys, the blood vessels, etc.

The invention is further illustrated by the following Examples:

EXAMPLE 1

A solution of gas filled microbubbles stabilised by a phospholipids interface was prepared according to Example 1 of U.S. Pat. No. 5,445,813. The dry matter concentration was 5 mg/ml in a saline solution (0.9% NaCl). Typically, the bubble size distribution extended from 0.2 to 15 μm. The concentration of bubbles between 2 and 5 μm was $5\times10^7$ microbubble/ml.

The solution was transferred in a 50 ml plastic syringe and samples were taken in time intervals for analysis. This represent the starting 100% of the bubble concentration. The syringe was mounted in the infusion unit and the elution started. The elution flow was fixed at 1.6 ml/min.

Aliquots of the eluted solution were analysed by Coulter measurement (bubbles distribution; size and concentration) and imaging.

TABLE 1

| Radius | Va |
|---|---|
| 1.0 | 0.131 |
| 1.5 | 0.294 |
| 2.0 | 0.523 |
| 2.5 | 0.817 |
| 3.0 | 1.177 |
| 3.5 | 1.602 |
| 4.0 | 2.092 |
| 4.5 | 2.648 |
| 5.0 | 3.269 |
| 5.5 | 3.955 |
| 6.0 | 4.707 |
| 6.5 | 5.524 |
| 7.0 | 6.407 |
| 7.5 | 7.355 |
| 8.0 | 8.368 |
| 8.5 | 9.446 |
| 9.0 | 10.590 |
| 9.5 | 11.800 |
| 10.0 | 13.075 |
| 10.5 | 14.415 |
| 11.0 | 15.820 |
| 11.5 | 17.291 |
| 12.0 | 18.828 |
| 12.5 | 20.429 |
| 13.0 | 22.096 |
| 13.5 | 23.829 |
| 14.0 | 25.626 |
| 14.5 | 27.489 |

In water, the rate of rise (Va) by buoyancy of air filled microbubbles of radius (a) can be obtained from the following Stokes relation $$Va = \frac{2gr}{9h} \times a^2$$

where g is the gravitation constant (9.81 ms$^{-2}$), r is the density of water (1000 g/l) and h is the viscosity ($10^{-3}$ Kg[s·m]). Table 1 shows a range of such rates (in mm/min) in function to the bubble radius in μm. The tangential speed ($V_r = 2$ pnR) of a syringe barrel of 28 mm diameter (R=14 mm) in function to the rotation rpm (n) is given in the next Table 2.

TABLE 2

| n (rpm) | $V_r$ (mm/min) |
|---|---|
| 0.5 | 2539 |
| 1 | 5278 |
| 2 | 10556 |
| 3 | 15834 |
| 4 | 21112 |
| 5 | 26389 |
| 10 | 52779 |

It is seen from the foregoing figures that in the case of a suspension of microbubbles of size in the range of 1–10 µm, very low rates of rotation of the syringe are sufficient to prevent segregation of the bubbles by buoyancy. This means that even at low rates of rotation the tangential speed of the microbubbles in suspension is much larger than buoyancy and that the microbubbles will move together with the rotating liquid and will not rise to the top of the syringe.

In a comparative study, the syringe was rotated along its axis in an alternative mode at a speed of 60 rpm. The results were compared with an experiment where the syringe was not rotated (under otherwise same experimental conditions).

Figure 2:
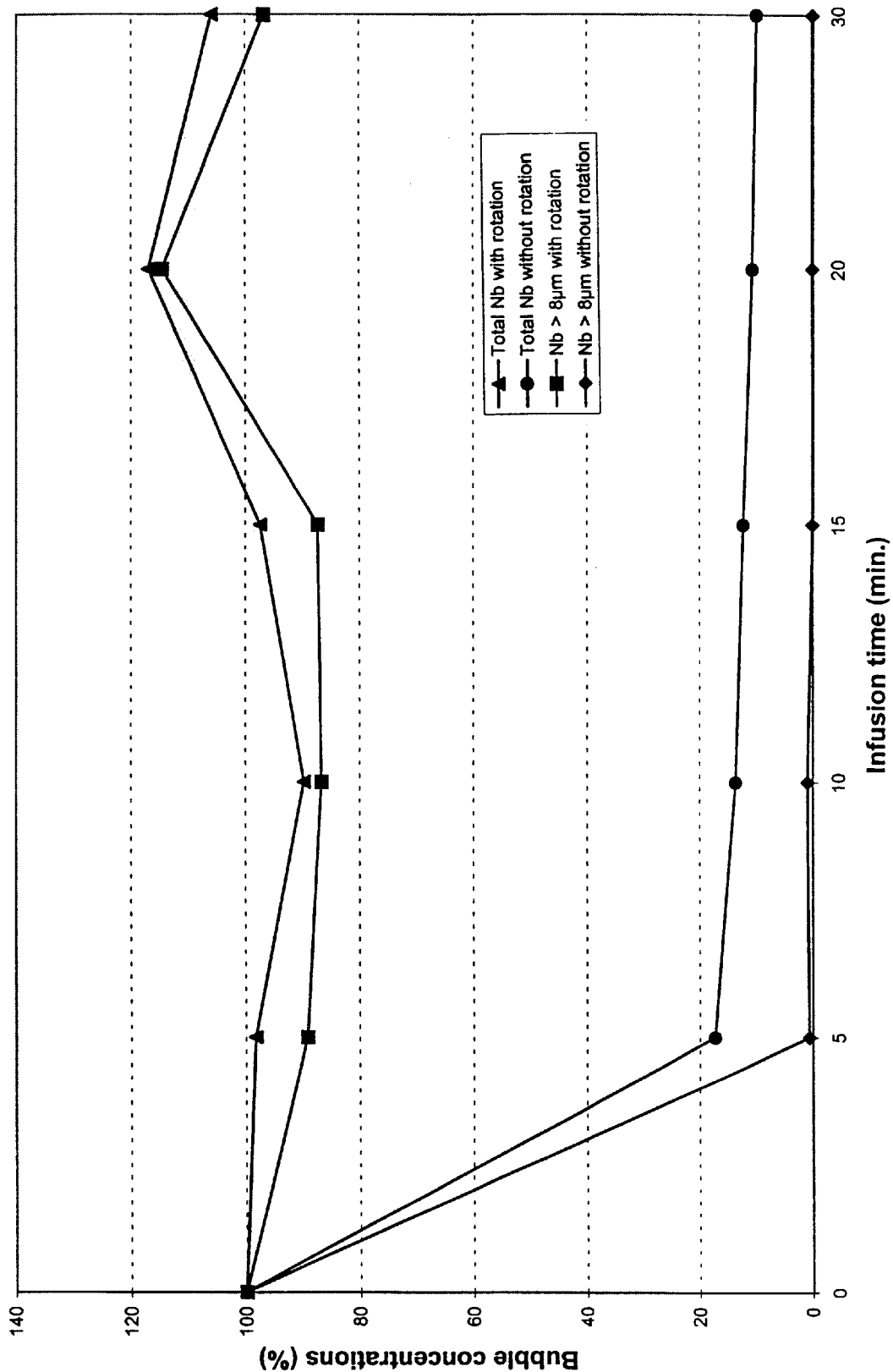
FIG. 2 is a graph illustrating the homogeneity variations in a suspension of microbubbles contained in a syringe, the latter being either still or subjected to motion according to the invention.
Figure 3:
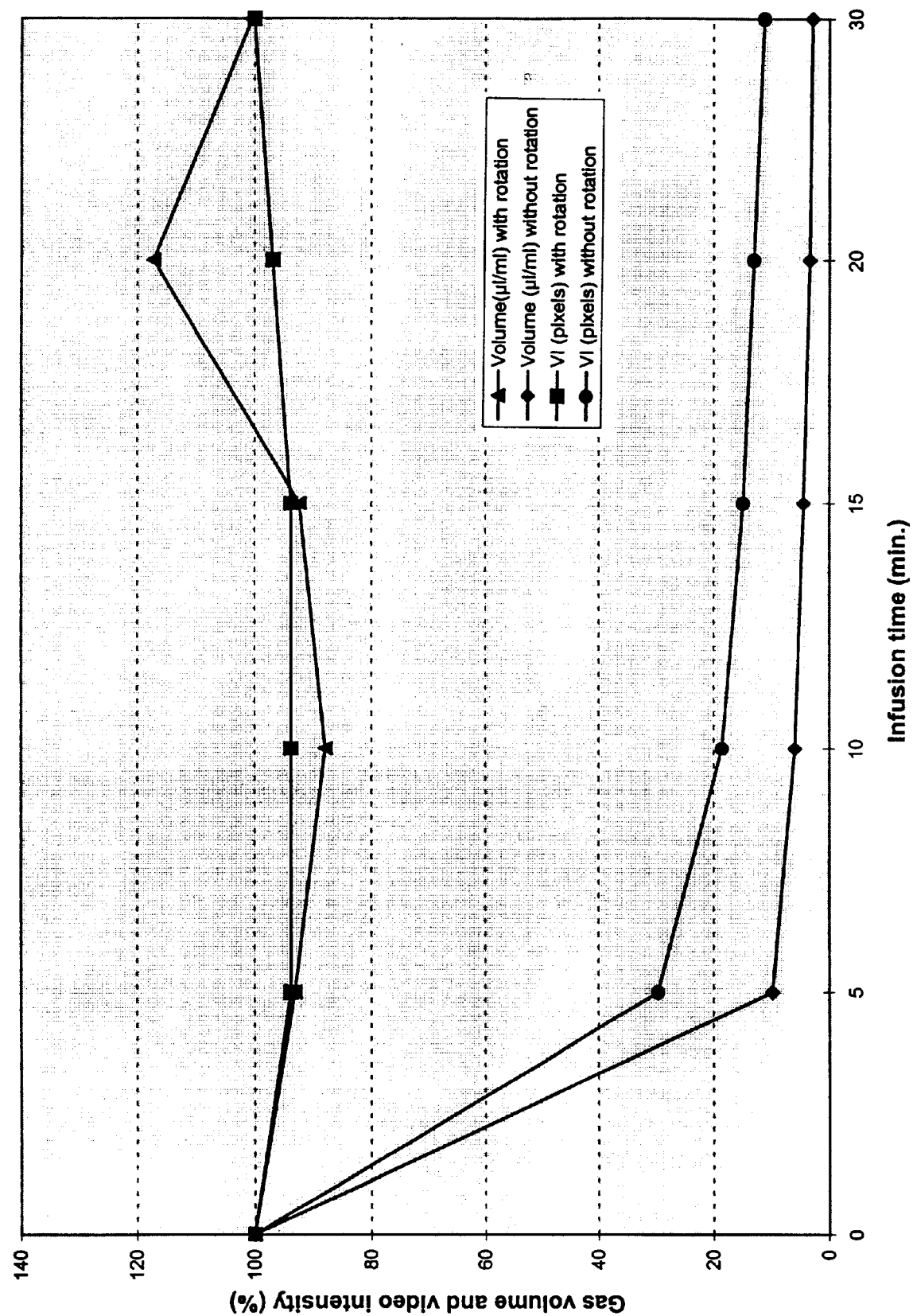
FIG. 3 is a graph illustrating the gas volume and in vitro intensity of samples with and without treatment according to the invention.

FIG. 2 shows the evolution of the concentration of the total microbubble population and, separately, microbubbles above 8 µm along the elution while FIG. 3 shows the evolution of imaging intensity and the total bubble volume in the course of elution. In the case of no-agitation, the concentration decreases rapidly due to decantation. At the end of the infusion, the concentration rises sharply (not shown) because all the bubbles accumulate in the upper part of the barrel.

When the syringe is rotated, the bubble concentration remains constant throughout the entire infusion.

The same type of experiments were carried out under different experimental conditions including different microbubbles sizes and concentrations, different elution rates, different rotation types and speed, different syringe types and different particles such as heavy magnetite particles or other microbubble structures including phospholipid, tripalmitin or albumin encapsulated microbubbles. All experiments invariably showed that the method of infusion disclosed delivers homogeneous suspensions of active agents.

EXAMPLE 2

Preparation of Contrast Agents for Infusion

To test the efficiency of the present invention (a system of rotary syringe pump), different contrast agents for ultrasound echography were prepared.

Microbubble Suspensions

Phospholipid stabilised microbubbles were obtained in the following manner. 500 mg DAPC and 50 mg DPPA (Avanti Polar Lipids, Inc.) were dissolved in hexane/isopropanol 8/2 (v/v) and dried in a round-bottomed flask using a rotary evaporator and, further, in a vacuum dessicator. After addition of water (100 ml), the suspension of lipids was heated at 75° C. for 1 hour under agitation and then extruded through a 0.8 µm polycarbonate filter (Nuclepore®). The resulting suspension and 10 g of polyethyleneglycol ($M_W$4000) were mixed and lyophilised. 2 g of the lyophilisate was introduced into a glass vial and sealed under $SF_6$ or an air/$C_4F_{10}$ mixture. After reconstitution with 25 ml NaCl 0.9%, the resulting suspensions contained about $6 \times 10^8$ ($SF_6$) or $1 \times 10^9$ ($C_4F_{10}$) bubbles per ml with a mean diameter in number of 2 µm (Coulter Multisizer).

Microballoon Suspensions

Gas filled albumin microspheres were prepared as described by Porter T. R. (J. Am. Coll. Cardio. 23 (1994) 1440 and PCT/WO 96/38180). 16 ml of human serum albumin (HSA) diluted 1:3 with dextrose (5%) was introduced into a 20 ml syringe and sonicated (sonifier 250 Branson) for 80 seconds in the presence of a flux of $C_3F_8$ gas (octafluoropropane) at liquid/air interface. The sonicator tip was immersed at about 1 cm below the surface of the solution, the ultrasound energy level was set at output −40 and the temperature of the solution was monitored at 75° C. After removing the foam phase by decantation, the final suspension contained $8 \times 10^8$ gas microspheres per milliliter with a mean diameter in number of 2 µm (9 µm in volume) determined by Coulter®. The suspensions are stored at 4° C. until use.

EXAMPLE 3

Determination of the Limit of Rotation Rate for the Syringe used for Infusion

The effect of syringe rotation on stability of gas microbubble suspensions in the syringe used for infusion has been tested using a 50 ml syringe which was mounted on a rotation system which allows very low rotation speeds (about 1 rpm). Prior to its mounting the syringe was filled with 30 ml of phospholipid stabilised microbubble suspension. The mounted syringe was then rotated at different speeds: 0 (no rotation) 1.3, 2 and 60 rpm (1 Hz) and the suspension monitored taking one sample every 5 minutes. The samples were then analysed using Coulter counter. Table 3A shows the results obtained with a suspension of $3.1 \times 10^8$ microbubbles/ml having a mean diameter of 2.1 µm.

TABLE 3A

Homogeneity of microbubble suspensions in the syringe as a function of the rotation rate and time
(microbubble concentration 3.1 × $10^8$ bubbles/ml)

| | Syringe rotation rates | | | | | | | | | | | |
|---|---|---|---|---|---|---|---|---|---|---|---|---|
| rpm | 0 | 1.3 | 2 | 60 | 0 | 1.3 | 2 | 60 | 0 | 1.3 | 2 | 60 |
| Vr | 0 | 114 | 176 | 5278 | 0 | 114 | 176 | 5278 | 0 | 114 | 276 | 5278 |
| t (min) | Nb total (%) | | | | Nb > 8µ (%) | | | | Volume (%) | | | |
| 0 | 100 | 100 | 100 | 100 | 100 | 100 | 100 | 100 | 100 | 100 | 100 | 100 |
| 5 | 68.7 | 77.6 | 90.4 | 97.4 | 23.5 | 48.0 | 73.3 | 95.4 | 37.5 | 55.6 | 80.4 | 97.7 |
| 10 | 53.7 | 77.3 | 88.8 | 100.6 | 1.1 | 43.9 | 70.9 | 98.9 | 19.8 | 44.8 | 73.3 | 99.4 |
| 15 | 48.2 | 72.8 | 89.5 | 96.2 | 1.9 | 38.0 | 74.1 | 96.5 | 14.5 | 44.0 | 75.7 | 98.1 |
| 20 | 43.5 | 73.8 | 86.6 | 99.0 | 0.8 | 37.2 | 77.9 | 97.3 | 10.8 | 42.5 | 73.6 | 98.6 |

TABLE 3A-continued

Homogeneity of microbubble suspensions in the syringe as a function of the rotation rate and time (microbubble concentration $3.1 \times 10^8$ bubbles/ml)

Syringe rotation rates

| 25 | 39.9 | 76.4 | 88.5 | 100.3 | 0.5 | 36.9 | 84.6 | 99.5 | 9.6 | 43.0 | 81.6 | 99.7 |

Nb total (%): percentage of the total bubble concentration as compared to value at t = 0.
Nb > 8μ(%): percentage of the bubbles above 8 μm as compared to value at t = 0.
Volume (%): percentage of total bubble volume per ml of solution as compared to value at t = 0
rpm: rotation per minute; Vr
(mm/min) = tangential speed of the syringe (radius = 14 mm)
Gas microbubbles: air/$C_4F_{10}$ (50:50).

The above results clearly indicate that even at very low rotation rates (1.3 and 2 rpm), the buoyancy rise of the microbubbles is prevented. This is because even at low rotation rates, the tangential velocity of the microbubble is far greater than that of buoyancy. As previously shown, microbubbles of 3 and 10 μm have the respective rising rates of 0.29 and 3.3 mm/min. At 1.3 rpm rotation, the tangential speed is 114 mm/min (Vr=2p×rpm×$R_{syringe}$) which makes the tangential component of the 3 μm microbubble 390 times greater than the buoyancy. For 10 μm microbubble the tangential component is 35 times greater than the ascension rate. It should be mentioned that at very high rotation rates (e.g. 1,000 rpm) the microbubbles will concentrate in the middle of the syringe (as the radial component becomes dominant). Rotational speeds at which the radial component becomes important are not of interest as under such conditions the suspension becomes non-homogeneous again. The rotational speed at which the radial force is becoming significant depends on the syringe size (diameter, size of microbubbles and viscosity of the suspension) hence the exact value of the rotational speed at which the radial component becomes important is to be established for each individual case. However, as already pointed out such rotational speeds are to be avoided.

However, the lower limit of the syringe rotation is not easy to determine as the microbubble ascention rate is also a function of viscosity and density of the suspension, the nature of the gas used, the microbubble diameter and size distribution as well as the type of the microparticles (i.e. microbubbles having just a layer of a surfactant stabilising the gas, microballoon with a tangible membrane or microemulsion).

EXAMPLE 4
Evaluation of the Efficiency of the Rotary Pump
A. Infusion of Gas Microbubble Suspensions at Low Bubble Concentration and "fast" Infusion Rate (3.3 ml/min)

In this study, the phospholipid stabilised gas microbubbles were prepared with a gas mixture (air/perfluorobutane 50:50) as gas phase.

The efficacy of the rotary pump of the present invention was evaluated by checking the homogeneity and stability of the bubble suspensions during the infusion. During a continuous infusion, the bubble suspensions were successively sampled at different infusion times with an interval of about every 5 minutes. The syringe used for infusion had a effective volume of 60 ml with a diameter of 28 mm (Braun Perfusor, Germany). The rotation rate of the syringe was

TABLE 3B

Homogeneity of microbubble suspensions in the syringe as a function of the rotation rate and time (microbubble concentration $1.3 \times 10^9$ bubbles/ml)

| | Syringe rotation rates | | | | | | | | | | | |
|---|---|---|---|---|---|---|---|---|---|---|---|---|
| rpm | 0 | 3 | 12 | 60 | 0 | 3 | 12 | 60 | 0 | 3 | 12 | 60 |
| Vr | 0 | 264 | 1056 | 5278 | 0 | 264 | 1056 | 5278 | 0 | 264 | 1056 | 5278 |
| t (min) | Nb total (%) | | | | Nb > 8μ (%) | | | | Volume (%) | | | |
| 0 | 100 | 100 | 100 | 100 | 100 | 100 | 100 | 100 | 100 | 100 | 100 | 100 |
| 5 | 6.0 | 26.0 | 76.8 | 81.3 | 0.5 | 16.0 | 73.1 | 83.4 | 1.5 | 17.2 | 81.4 | 87.7 |
| 10 | 3.2 | 26.3 | 78.8 | 81.3 | 0.2 | 19.1 | 71.5 | 79.9 | 1.0 | 20.0 | 81.9 | 79.4 |
| 15 | 3.9 | 27.3 | 81.5 | 82.2 | 0.6 | 16.8 | 78.0 | 80.5 | 1.1 | 20.3 | 84.9 | 90.8 |
| 20 | 4.3 | 32.0 | 76.6 | 95.0 | 0.2 | 19.2 | 79.6 | 85.9 | 1.8 | 21.5 | 92.3 | 92.6 |
| 25 | 0 | 31.7 | 78.9 | 95.3 | 0 | 16.9 | 78.6 | 85.5 | 0 | 18.4 | 83.4 | 91.1 |

Nb total (%): percentage of the total bubble concentration as compared to value at t = 0.
Nb > 8μ (%): percentage of the bubbles above 8 μm as compared to value at t = 0.
Volume (%): percentage of total bubble volume per ml of solution as compared to value at t = 0
rpm: rotation per minute;
Vr (mm/min) = tangential speed of the syringe (radius = 14 mm)
Gas microbubbles: air/$C_4F_{10}$ For more concentrated suspensions (e.g. $1.3 \times 10^9$ bubbles/ml) the microbubble ascension rate increases in the syringe. This is probably due to microbubble interactions (associations, dragg etc.) indicating that higher rotation speeds are required for prevention of microbubble ascension in the suspensions with higher microbubble concentrations.

fixed at 60 rpm or 1 Hz (in order to compare different suspensions) and the direction of rotation was reversed for each turn. Infusion was stopped after 15 minutes while maintaining syringe rotation and then restored at the same rate during one minute after 30 minutes and 60 minutes. The bubble concentration, sizes and size distribution were assessed with Coulter® Multisizer II and the echo contrast effect of the suspensions was simultaneously examined with an echographic imaging device (Acuson 128XP10, USA). For Coulter® and echo evaluation, the native samples taken from the syringe were further diluted 1000 and 3000 folds (in some experiences 1/750). For in vitro imaging evaluation, an acoustic phantom ATS (Peripheral Vascular Doppler Flow Phantom, ATS Laboratoies Inc., USA) was used and the image was visualised in B-mode with a 3.5 MHz ultrasound probe. The acoustic energy was set to minimum (−9 dB) in order to prevent bubble destruction. The results are summarised in the Table 4.

TABLE 4

Evaluation of the efficacy of the rotary pump
(Coulter and Echo imaging)
Gas microbubbles: air/$C_4F_{10}$
Pump flow rate: 3.3 ml/min

| t (min) | Nbtot/ ml × $10^8$ | Nb > 8μ/ ml × $10^6$ | Diam (μm) | Vol/ml | VI (pixels) |
|---|---|---|---|---|---|
| 0 | 3.26 | 4.90 | 2.09 | 7.33 | 62 |
| 2 | 2.97 | 4.90 | 2.15 | 7.12 | 59 |
| 8 | 3.31 | 4.50 | 2.06 | 7.15 | 59 |
| 15 | 3.06 | 3.55 | 2.09 | 5.82 | 59 |
| 30 | 3.12 | 4.82 | 2.15 | 6.96 | 59 |
| 60 | 3.15 | 4.66 | 2.10 | 7.03 | 59 |

Nb > 8μ/ml: number of bubbles above 8 μm.
Nb total/ml: total bubble concentration.
Volume (μl/ml): total bubble volume per ml of solution
Diameter (μm): mean diameter in number.
VI: video intensity (dilution 1:3000)

These results show that even at a small rotation rate (1 Hz), the bubble suspension was fairly stable and homogeneous: both the total bubble count and bubbles >8 μm remain constant during the entire infusion.

B. Infusion of Gas Microbubble Suspensions at High Bubble Concentration and "slow" Infusion Rate (1.2 ml/min)

The example A was repeated at a "slow" infusion rate and a higher concentration of the microbubbles. One can note from the Table 5 that even at very slow infusion rate (corresponding to 0.017 ml/kg/min for a 70 kg person) and a very high bubble concentration (Nb/ml>$10^9$/ml), the present rotary infusion pump is capable to ensure the stability and the imaging performance of the bubble suspensions during the entire infusion (24 min).

TABLE 5

Evaluation of the efficacy of the rotary pump
(Coulter and Echo imaging)
Gas microbubbles: air/$C_4F_{10}$
Pump flow rate: 1.2 ml/min

| t (min) | Nb/ml × $10^9$ | Nb > 8μ/ ml × $10^7$ | Diameter (μm) | Volume/ml | VI (pixels) |
|---|---|---|---|---|---|
| 0 | 1.10 | 2.2 | 2.09 | 32.5 | 60 |
| 5 | 1.03 | 2.2 | 2.15 | 30.9 | 60 |
| 13 | 1.01 | 2.1 | 2.06 | 30.5 | 55 |
| 18 | 1.03 | 2.1 | 2.09 | 30.0 | 58 |
| 24 | 1.04 | 2.1 | 2.15 | 30.5 | 57 |

Nb > 8μ/ml: number of bubbles above 8 μm.
Nb total/ml: total bubble concentration.
Volume (μl/ml): total bubble volume per ml of solution
Diameter (μm): mean diameter in number.
VI: video intensity (dilution 1:3000)

EXAMPLE 5

Evaluation of the Efficacy of the Rotary Pump—Comparative Tests with and without Syringe Rotation The procedure of Example 4 was repeated except that the phospholipid stabilised microbubbles were prepared with gas $SF_6$ instead of air/$C_4F_{10}$. Moreover, the stability of the gas bubble suspensions during infusion was compared using the same pump in the presence and absence of rotation of the syringe (R=28 mm, rotation rate=60 rpm and 0 rpm). The experimental results of a concentrated bubble suspension (Nb>$10^9$/ml) infused at an infusion rate of 1.1 ml/min are shown in Table 6. Without syringe rotation, the amount of microbubbles delivered from the syringe decrease rapidly during infusion, especially for the large bubbles (see Nb>8 μm and the volume). After 5 minutes of infusion, the total bubble concentration decreased by 83%, >99% for the bubbles larger than 8 μm and 90% for the bubble volume. After 10 minutes, the video intensity had decreased by a factor 3 and the contrast effect of the microbubbles was almost non detectable (IV=6±3 pixels for the background) at 10 minutes of the infusion. In contrast, in the presence of rotation the bubble suspension remained stable during the entire infusion (30 min).

TABLE 6

Evaluation of the efficacy of the rotary pump: comparative test
Gas microbubbles: $SF_6$
Pump flow rate: 1.1 ml/min

| | Coulter measurement | | | | | | | | Imaging | |
|---|---|---|---|---|---|---|---|---|---|---|
| t (min) | Nb/ml × $10^9$ | | Nb > 8μ/ml × $10^7$ | | Diamter (μm) | | Volume/ml | | VI (pixels) | |
| rot | with | w/out | with | w/out | with | w/out | with | w/out | with | w/out |
| 0 | 1.2 | 1.1 | 1.58 | 1.32 | 2.09 | 2.22 | 24.3 | 20.4 | 32 | 54 |
| 5 | 1.16 | 0.19 | 1.41 | 0.008 | 2.09 | 2.14 | 22.6 | 2.0 | 30 | 16 |
| 10 | 1.06 | 0.15 | 1.37 | 0.012 | 2.13 | 1.96 | 21.4 | 1.2 | 30 | 10 |
| 15 | 1.15 | 0.13 | 1.38 | 0.00 | 2.11 | 1.92 | 22.5 | 0.9 | 30 | 8 |

TABLE 6-continued

Evaluation of the efficacy of the rotary pump: comparative test
Gas microbubbles: $SF_6$
Pump flow rate: 1.1 ml/min

| t (min) | Coulter measurement | | | | | | | | Imaging | |
|---|---|---|---|---|---|---|---|---|---|---|
| | $Nb/ml \times 10^9$ | | $Nb > 8\mu/ml \times 10^7$ | | Diamter ($\mu$m) | | Volume/ml | | VI (pixels) | |
| rot | with | w/out | with | w/out | with | w/out | with | w/out | with | w/out |
| 20 | 1.38 | 0.12 | 1.81 | 0.00 | 2.13 | 1.83 | 28.5 | 0.7 | 31 | 7 |
| 30 | 1.25 | 0.11 | 1.53 | 0.00 | 2.11 | 1.79 | 24.4 | 0.6 | 32 | 6 |

$Nb > 8\mu/ml$: number of bubbles of 8 $\mu$m.
Nb total/ml: total bubble concentration.
Volume ($\mu$l/ml): total bubble volume per ml of solution
Diameter ($\mu$m): mean diameter in number.
VI: video intensity (dilution 1:3000)

TABLE 7

Evaluation of the efficacy of the rotary pump: comparative tests
Gas microbubbles: $SF_6$
Pump flow rate: 3.3 ml/min

| t (min) | Coulter measurements | | | | | | | | | |
|---|---|---|---|---|---|---|---|---|---|---|
| | $Nb\ tot/ml \times 10^6$ | | $Nb > 8\mu/ml \times 10^6$ | | Diam. ($\mu$m) | | Vol./ml | | Vol % | |
| rotat | with | w/out | with | w/out | with | w/out | with | w/out | with | w/out |
| 0 | 2.73 | 2.48 | 3.14 | 2.99 | 2.22 | 2.09 | 5.5 | 4.9 | 100.0 | 89.4 |
| 5 | 2.57 | 2.05 | 3.21 | 0.5.4 | 2.23 | 1.94 | 5.3 | 2.1 | 96.7 | 39.1 |
| 10 | 2.53 | 1.71 | 3.42 | 0.01 | 2.27 | 1.81 | 5.8 | 1.1 | 105.7 | 20.6 |
| 15 | 2.48 | 1.41 | 3.28 | 0.00 | 2.28 | 1.64 | 5.2 | 0.6 | 96.1 | 10.8 |
| 20 | 2.35 | 1.16 | 1.33 | 0.00 | 2.21 | 1.54 | 4.6 | 0.5 | 83.6 | 8.3 |

$Nb > 8\mu/ml$: number of bubbles above 8 $\mu$m.
Nb total/ml: total bubble concentration.
Volume ($\mu$l/ml): total bubble volume per ml of solution
Diameter ($\mu$m): mean diameter in number.
VI: video intensity (dilution 1:3000)

In Table 7, the comparative infusion was conducted at a lower bubble concentration ($2.7\ 10^8$/ml) and an infusion rate of 3.3 ml/min. Again, these results show a very good efficacy of the rotary infusion system to maintain the homogeneity and stability of the microbubble suspensions during infusion. In contrast, the syringe pump without rotation was completely inadequate for microbubble infusion.

EXAMPLE 6
Evaluation of the Efficiency of the Rotary Pump Application to Gas Microspheres (Comparative Tests)

The Example 5 was repeated with the gas albumin microspheres prepared as described in Example 2. For the infusion, the bubble concentration was adjusted to $6\times10^8$/ml by diluting the suspension with HSA/dextrose (1:3). In the present experience, the in vitro characteristics of the microspheres during infusion (2.7 ml/min) with and without the syringe rotation were compared to assess the homogeneity of the suspensions delivered from the syringe. The results are gathered in Table 8.

TABLE 8

Evaluation of the efficacy of the rotary infusion pump with gas albumin microspheres
Gas microbubbles: $C_3F_8$
Pump flow rate: 2.7 ml/min

| t (min) | $Nb\ tot/ml \times 10^8$ | | $Nb > 8\mu/ml \times 10^6$ | | Diam ($\mu$m) | | Vol/ml | | VI (pixels) | |
|---|---|---|---|---|---|---|---|---|---|---|
| rot | with | w/out | with | w/out | with | w/out | with | w/out | with | w/out |
| 0 | 6.64 | 6.7 | 9.6 | 7.6 | 2.03 | 1.97 | 15.4 | 12.3 | 47 | 46 |
| 5 | 6.4 | 6.6 | 8.0 | 4.5 | 1.96 | 1.93 | 13.1 | 8.8 | 47 | 38 |
| 10 | 6.4 | 6.3 | 6.0 | 2.6 | 1.91 | 1.8 | 10.3 | 5.0 | 45 | 23 |
| 15 | 6.4 | 6.0 | 6.5 | 0.38 | 1.92 | 1.65 | 10.5 | 3.5 | 45 | 19 |

TABLE 8-continued

Evaluation of the efficacy of the rotary infusion pump with gas albumin microspheres
Gas microbubbles: $C_3F_8$
Pump flow rate: 2.7 ml/min

| t (min) | Nb tot/ml × $10^8$ | | Nb > 8μ/ml × $10^6$ | | Diam (μm) | | Vol/ml | | VI (pixels) | |
|---|---|---|---|---|---|---|---|---|---|---|
| rot | with | w/out | with | w/out | with | w/out | with | w/out | with | w/out |
| 20 | 6.25 | 5.2 | 6.15 | 0.15 | 1.92 | 1.61 | 9.9 | 3.8 | 43 | 26 |

Nb > 8μ/ml: number of bubbles above 8 μm.
Nb total/ml: total bubble concentration.
Volume (μl/ml): total bubble volume per ml of solution
Diameter (μm): mean diameter in number.
VI: video intensity (dilution 1:3000)
Background: VI = 9 pixels The albumin microspheres appear to be more homogeneous in the syringe than phospholipid microbubbles in the absence of rotation. This is likely to be due to the higher viscosity of the albumin/dextrose solution (5%) and possibly to the thicker wall of the microspheres (about 15 times thicker than a phospholipid monolayer). Nevertheless, large microspheres (>8 μm) still decanted in the syringe and their concentration decreased progressively during infusion. After 10 minutes, the volume of microspheres and the video intensity decreased to half of the initial values. It was been reported that the myocardial perfusion with a similar agent—FSO69 (Optison®, HSA-$C_3F_8$ microsphere suspensions) was attributed essentially to a small number of large microspheres (10–15 μm) entrapped in the tissue (Skyba et al., *J. Am. Coll. Cardio.* 28 (1996) 1292–1300). Therefore, on can speculate that for such clinical application this kind of contrast agents could hardly be infused by a classic infusion pump as demonstrated in the present example.

EXAMPLE 7

Tetracaine filled tripalmitin microcapsules made according to Example 6 of WO96/15815 were suspended in 50 ml of saline solution (0.9% NaCl). The suspension with a concentration of tetracaine of 0.06 mg/ml was placed into a 50 ml syringe. The syringe was placed on the rotational pump of the invention and the exit concentration of tetracaine measured using UV spectrophotometer (in THF/water 60/40% at 307 nm). The syringe was rotated at a rate of 1 Hz (alternating direction of rotation every 180°). The rate of infusion was 1.5 ml/min. The UV analysis showed constant concentration of tetracaine over the entire period of infusion. In the parallel experiment in which the tetracaine filled syringe was kept stationary the exit concentration of the medicament varied with time.

EXAMPLE 8

Fifty milligrams of Amphotericin B in the deoxycholate form (Fungizone® Bristol Mayers Squibb) were dispersed in 50 ml of Intralipid® 20% (Pharmacia) and the emulsion obtained (Chavanet, P,. *Rev. Med. Interne* 18 (1997) 153–165) introduced into a 50 ml syringe. The syringe was placed on the rotational pump and infused at 1 ml/min rate and rotation of 1 Hz (alternating direction of rotation every 360°. Exit concentration of Amphotericin B was followed by HPLC (detection UV/visible at 405 nm). The HPLC analysis confirmed constant concentration of the medicament during the entire infusion. The experiment clearly showed that the separation of Amphotericin B reported by several research groups (Trissel, L. A., *Am. J. Health Syst. Pharm.* 52 (1995) 1463; Owens, D., *Am. J. Health Syst. Pharm.* 54 (1997) 683) was successfully suppressed using the method disclosed.

EXAMPLE 9

A liposome solution was prepared from 9/1 molar ratio of hydrogenated soy lecithin (DPPC) and dipalmitoylphosphatidic acid disodium salt (DPPA) in chloroform according to a well known procedure (e.g. EP 0 514 523). After extrusion and cooling of MLV suspension the same was concentrated to 30 mg/ml by microfiltration. To 1 l of the concentrated liposome solution, 1 l of an aqueous solution containing 1040 g of (S)-N,N'-bis [2-hydroxy-1-(hydroxymethyl)-ethyl]-2,4,6-triiodo-5-lactamido-isophtalamide (Iopamidol®, an X-ray contrast agent of BRACCO S.p.A.) was added and the resulting mixture having an iodine concentration of 260 g/l was incubated. The density of the Iopamidol® solution was 1.29 g/cm$^3$.

An aliquot of the liposome preparation was dialyzed against saline (NaCl 0.9% in water) until all iopamidol outside the liposomes vesicles was removed. The iodine-to-lipid ratio of the preparation obtained (I/L) was between 3 and 5 mg of entrapped iodine per mg lipid.

Part of the preparation of contrast agent-loaded liposomes was introduced into a syringe which was placed on the rotational pump of the invention and the exit concentration of the contrast agent measured using HPLC. The syringe was rotated at a rate of 1 Hz (alternating direction of rotation every 180°). The rate of infusion was 1.5 ml/min. The HPLC analysis showed constant concentration of the iodinated contrast agent over the entire period of infusion.

When, in the foregoing example, the Iopamidol was replaced by Iomeprol (N,N'-bis(2,3-dihydroxypropyl)-2,4,6-triiodo-5-glycolamido-isophtal-imide), another iodinated contrast agent from BRACCO S.p.A., similar results were experienced.

What is claimed is:

1. An injector system for administering to patients by injection or infusion of a suspension of microparticles in an aqueous liquid carrier, said system in combination with said suspension comprising a syringe whose barrel contains said suspension of microparticles, and automatic electromechanical power means controllably acting on the syringe to inject the suspension of microparticles into a patient, wherein said injector system further comprises means for continuously rocking or rotating said syringe containing said suspension of microparticles during an entirety of said injection or infusion, said means for continuously rocking or rotating keeping said suspension of microparticles in the syringe homogenous by preventing segregation of the microparticles by gravity or buoyancy without damaging the microparticles or disturbing their distribution.

2. The combination of claim 1, in which said means for continuously rocking or rotating said syringe containing the suspension of microparticles comprise support means under continuous motion holding the syringe in the injection system, the effect of the motion applied to the support means being to agitate the suspension of microparticles in the syringe barrel during an entirety of the injection or infusion.

3. The combination of claim 2, in which the said motion applied to the support means and thus to the syringe is a rotation applied along or around the syringe longitudinal or transversal axis.

4. The combination of claim 3, in which the rotation applied to the syringe is alternatively in one and the opposite direction.

5. The combination of claim 4, in which each alternate rotation applied to the syringe covers an angle of 30°, 60°, 90°, 180°, 270° or 360°.

6. The combination of claim 3, wherein said support means under rotation are constituted by wheels in contact with the syringe barrel for driving it in consecutive rotation.

7. The combination of claim 3, in which the rotation applied to the syringe has a rotation rate from 0.5 to 200 rpm.

8. The combination of claim 2, in which the syringe containing the suspension of microparticles is provided with identification marks on the syringe.

9. The combination of claim 8, in which the identification marks are read through a laser detector, said laser detector being mobile or being fixed to the injector system.

10. The combination of claim 1, in which the suspension of microparticles is a contrast agent for ultrasonic imaging of patients.

11. The combination of claim 10, in which the contrast agent comprises, in suspension in an aqueous liquid carrier, gas filled microvesicles which are either microbubbles bounded by a gas/liquid interface made from dissolved surfactants, or microballoons bounded by a material envelope made of organic polymers, or of di- or tri-glycerides.

12. The combination of claim 11, in which the gas is a pure physiologically acceptable halogenated gas or gas mixture comprising at least one physiologically acceptable halogenated gas.

13. The combination of claim 12, in which the halogenated gas is selected from $CF_4$, $C_2F_6$, $C_3F_8$, $C_4F_8$, $C_4F_{10}$, $C_5F_{12}$, $C_6F_{14}$ or $SF_6$.

14. The combination of claim 12, wherein the gas mixture contains a gas selected from air, oxygen, nitrogen, helium, xenon or carbon dioxide.

15. The combination of claim 11, in which at least one of the surfactants is a saturated phospholipid in a lamellar or laminar form.

16. The combination of claim 15, in which at least one of the phospholipids is a diacyiphosphatidyl compound wherein the acyl group is a $C_{16}$ fatty acid residue or a higher homologue thereof.

17. The combination of claim 11, in which the polymer of the envelope is selected from polylactic or polyglycolic acid and their copolymers, denatured serum albumin, denatured hemoglobin, polycyanoacrylate, and esters of polyglutamic and polyaspartic acids.

18. The combination of claim 17, in which the microballoons are filled with $C_3F_8$ and the material envelope is made from albumin.

19. The combination of claim 11, in which the microballoons are bounded by saturated triglycerides, preferably tristearine, tripalmitine or mixtures of thereof with other glycerides, fatty acids and biodegradable polymers.

20. The combination of anyone of claim 1, in which the suspension of microparticles is a contrast agent for CT imaging.

21. The combination of claim 20, in which the contrast agent comprises as a suspension in a liquid carrier phase liposomes filled with an iodinated compound selected from iomeprol, iopamidol, iopentol, iohexol, metrizamide, iopromide, iogulamide, iosimide or ioversol.

22. Use of the combination of claim 21, in which iodine over lipid ratio I/L is 3 or more.

23. Use of the combination of claim 22, in which the imaging is ultrasonic imaging and the organ is at least one of the heart, the brain, the kidneys, and the liver.

24. The combination of claim 21, in which iodine over lipid ratio I/L is 3 or more.

25. The combination of claim 1 in which said automatic electromechanical power means acting on the syringe include a syringe plunger driven into forward or backward motion by helical screw means.

26. The combination of claim 25, in which the position of the plunger in the syringe is governed by a number of turns of said helical screw means as controlled by said automatic electromechanical power means.

27. The combination of claim 1, further comprising security means for automatically interrupting the injector operation in case of emergency.

28. The combination of claim 27, in which said security means operate by monitoring the force applied by the motor to the plunger of the syringe during injection, a sudden increase of that force producing a signal for stopping the injector operation.

29. Use of the combination of claim 1, in imaging of organs, blood vessels and tissue of a mammalian.

30. Use of the combination of claim 29, in which the imaging is CT image and the organ is the liver.

31. The combination of claim 1, wherein the means for continuously rocking or rotating the syringe rocks or rotates the syringe around the longitudinal axis of the syringe.

* * * * *